United States Patent [19]

Tseng

[11] 4,014,902
[45] Mar. 29, 1977

[54] INTERMEDIATE IN THE PROCESS FOR THE PREPARATION OF TRANS-$\Delta^9$-ISOAMBRETTOLIDE

[75] Inventor: Ching Y. Tseng, Middletown, N.J.

[73] Assignee: International Flavors & Fragrances Inc., New York, N.Y.

[22] Filed: June 9, 1976

[21] Appl. No.: 694,452

[52] U.S. Cl. .......................... 260/340.9; 252/522; 260/343; 260/348 C; 260/484 A; 260/486 D; 260/535 R; 260/539 R; 260/586 R; 260/617 R; 260/666 A

[51] Int. Cl.² ...................................... C07D 317/10

[58] Field of Search ........................... 260/340.9 R

[56] References Cited

UNITED STATES PATENTS 3,127,418  3/1964  Kuester .......................... 260/340.9

Primary Examiner—Ethel G. Love
Attorney, Agent, or Firm—Arthur L. Liberman; Franklin D. Wolffe

[57] ABSTRACT

A process is described for producing trans-$\Delta^9$-isoambrettolide from aleuritic acid in three reaction steps; first forming a dioxolane by treatment with an excess amount of an orthoformate or a dialkyl formamide dialkyl acetal; then forming the corresponding bengalene acid derivative by heating the dioxolane with acetic anhydride; and then cyclizing the resulting trans bengalene acid derivative by heating it, thereby yielding a high quality substantially pure or 100% pure trans-$\Delta^9$-isoambrettolide.

4 Claims, 3 Drawing Figures

IR SPECTRUM FOR EXAMPLE I(B): BENGALENE ACID METHYL ESTER

FIG.2
EXAMPLE I(C)
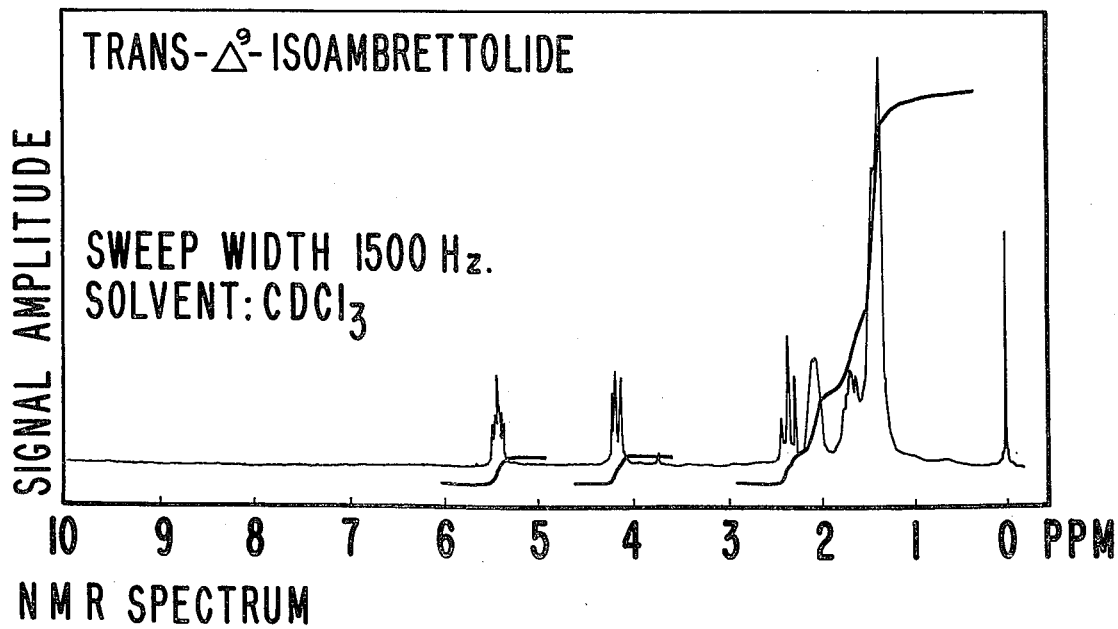
NMR SPECTRUM
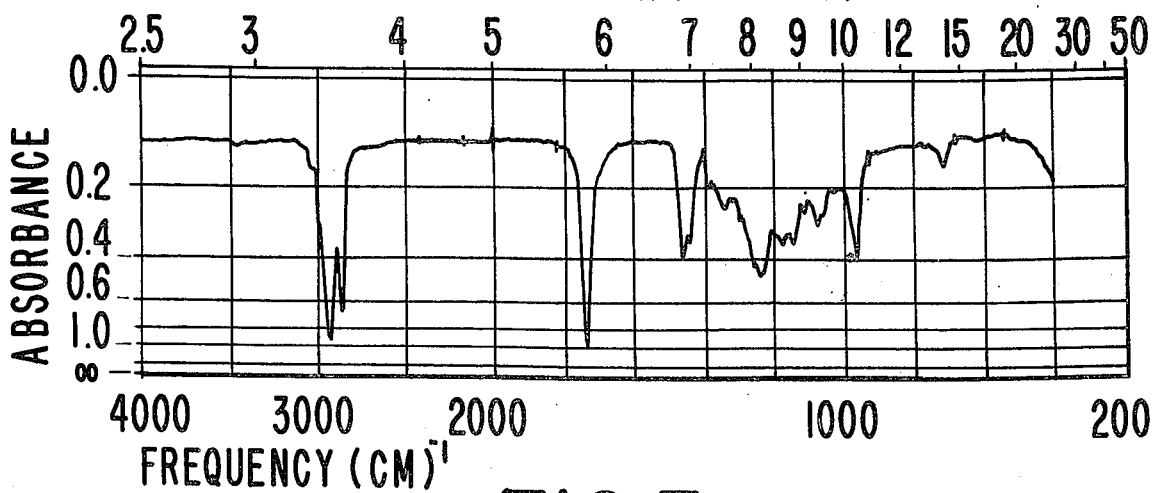
FIG.3

INTERMEDIATE IN THE PROCESS FOR THE PREPARATION OF TRANS-Δ⁹-ISOAMBRETTOLIDE

BACKGROUND OF THE INVENTION

This invention relates to a commercially feasible, efficient process for the preparation of a high quality substantially pure or 100% pure trans-$\Delta^9$-isoambrettolide for use in the perfume industry.

The macrocyclic compounds, i.e., trans-$\Delta^9$-isoambrettolide, prepared by the process of the present invention, are musk odorants and as such are highly desirable. The odor of musk is perhaps the most universally appreciated fragrance and is usually thought of as the animal note in perfumes. A number of naturally occurring species, both of animal and vegetable origin, possess musk odors; however, only three animal sources have achieved any commercial importance. It is because of the high demand and short supply of these naturally occurring musk odorants that numerous attempts have been made since the 1920's to synthesize compounds which would duplicate these desirable odors. Isoambrettolide has the formula:

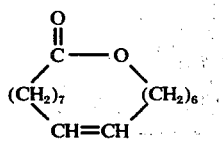

Ambrettolide has the formula:

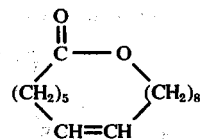

Ambrettolide itself naturally occurs in musk ambrette seed oil and is a valuable perfume base because of its desirable odor. Ruzicka and Stoll [Helv.Chem..Acta., 17, 1609(1928)] show a method for preparing macrocyclic lactones involving the oxidation of macrocyclic ketones with Caro's acid (persulfuric acid) to the corresponding lactones. Ambrettolide is said to be prepared by this method. U.S. Pat. No. 2,417,151 discloses a process for the preparation of ambrettolide involving intramolecular esterification. In this process sodium 6,16-dihydroxypalmitate is condensed with 1-chloropropanediol-2,3 to form the glycerol monoester which is treated with sodium acid sulfate to produce a mixture of unsaturated isomeric glycerol monoesters. This mixture is then distilled and worked up to yield a mixture of unsaturated isomeric large-ringed cyclic lactones including ambrettolide which can be separated out, if desired.

Trans-$\Delta^9$-isoambrettolide has preferably been produced from aleuritic acid by means of a much more complicated process; that is, by first forming the mono-acetate; then acetylating this mono-acetate; then mono-brominating the acylated aleuritic acid diacetate to form brombengal acid; dehydrohalogenating the brombengal acid using zinc to form bengalene acid; then, using ethylene glycol, trans-esterifying bengalene acid in the presence of a potassium glycolate catalyst whereby a poly-bengalene acid is formed, which is then trans-esterified to form trans-$\Delta^9$-isoambrettolide; but not in pure form. This reaction sequence is set forth schematically as follows:

1. STEP A - Preparation of Brombengal Acid

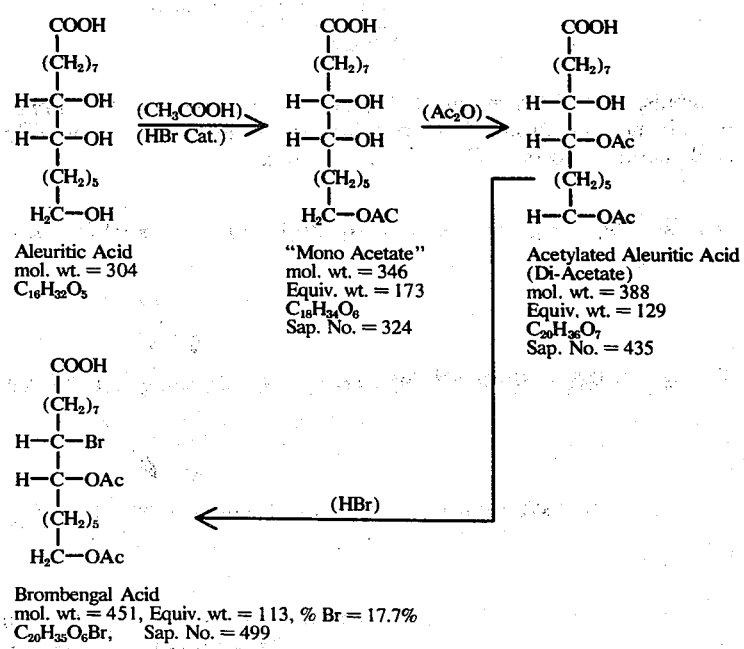

2. STEP B - Preparation of Bengalene Acid

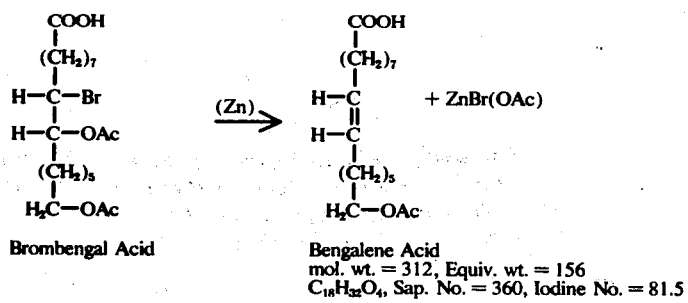

Brombengal Acid

Bengalene Acid
mol. wt. = 312, Equiv. wt. = 156
$C_{18}H_{32}O_4$, Sap. No. = 360, Iodine No. = 81.5

3. STEP C - CYCLIZATION AND CO-DISTILLATION OF AMBRETTOLIDE WITH GLYCERINE

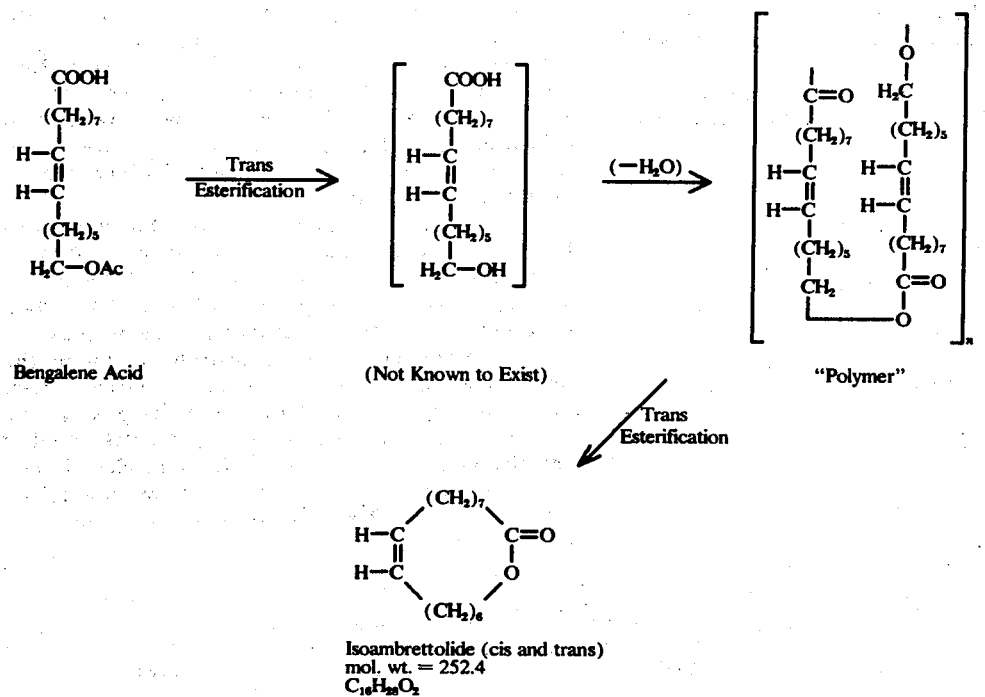

Bengalene Acid   (Not Known to Exist)   "Polymer"

Isoambrettolide (cis and trans)
mol. wt. = 252.4
$C_{16}H_{28}O_2$

Sabnis, et al., J.Chem.Soc. 1963, 2477-8, discloses a complicated synthesis of ambrettolide from aleuritic acid according to the following reaction scheme:

Another process for producing ambrettolide or iso-ambrettolide is set forth in U.S. Pat. No. 3,681,395,

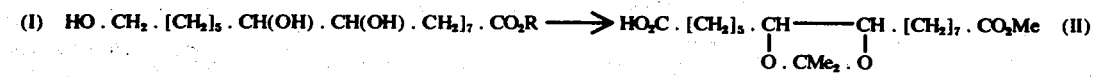

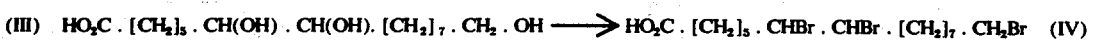

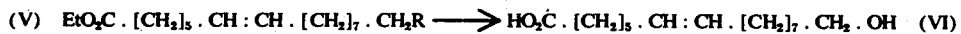

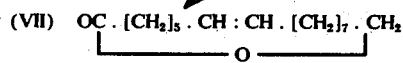

issued on Aug. 1, 1972 and this process discloses the following steps:

1. epoxidizing 1,9-cyclohexadecadiene of the structure

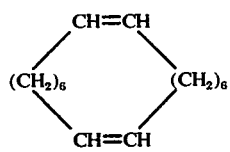

to form a diepoxidized cyclohexadecane of the structure

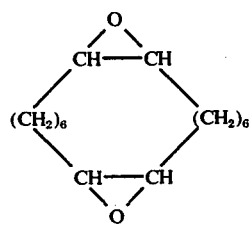

and 2. reducing said diepoxidized cyclohexadecane to form a mixture of cyclohexadecadiols of the structures

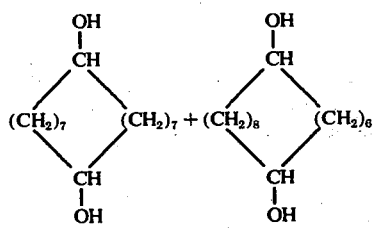

and 3. oxidizing said cyclohexadecadiols to form the corresponding hydroxy ketones of the structures

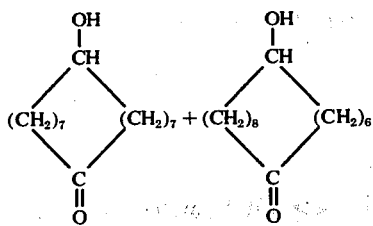

and 4. treating said hydroxy ketones with a peracid in the presence of a boron trifluoride etherate catalyst to form a mixture of hydroxy cyclohexadecanolides of the structures

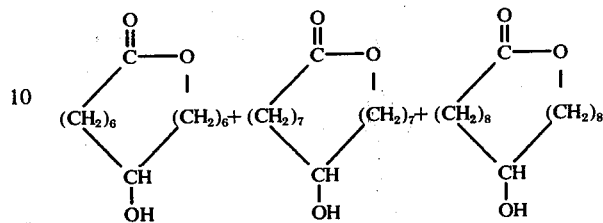

and 5. dehydrating said hydroxy cyclohexadecanolides to obtain the desired mixture of ambrettolide and isomers thereof of the general structure

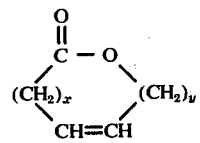

wherein $x$ is 5, 6, 7 and 8 and $y$ is 8, 7, 6 and 5, respectively and $x$ plus $y$ equals 13; said mixture can be separated by conventional means, if desired, into the various isomers, e.g., when $x$ is 5 and $y$ is 8 the lacetone is ambrettolide and when $x$ is 7 and $y$ is 6 the lactone is iso-ambrettolide.

However, nothing exists in the prior art showing a three step preparation from aleuritic acid easily to form substantially pure trans-$\Delta^9$-isoambrettolide.

Eastwood, et al., Tetrahedron Letters, No. 60, 5223-24, 1970, discloses a technique for converting 2-dimethylamino-1,3-dioxolane into alkenes according to the following reaction sequence:

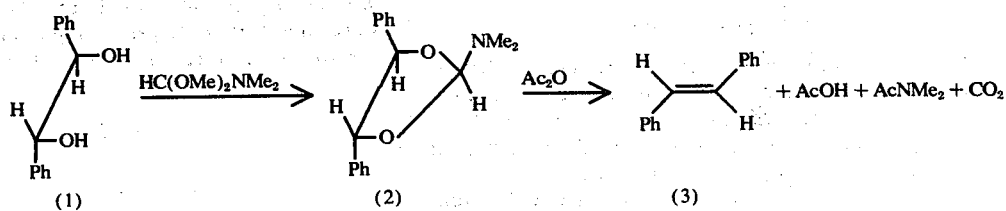

There is nothing in the Eastwood, et al. article which suggests that this reaction can be applied in the complicated process for producing trans-$\Delta^9$-isoambrettolide.

By the same token, Crank and Eastwood, Australian Journal of Chemistry, 1964, 17, 1392-8, discloses the introduction of a double bond in place of a diol moiety by use of a dioxolane intermediate according to the following reaction sequence:

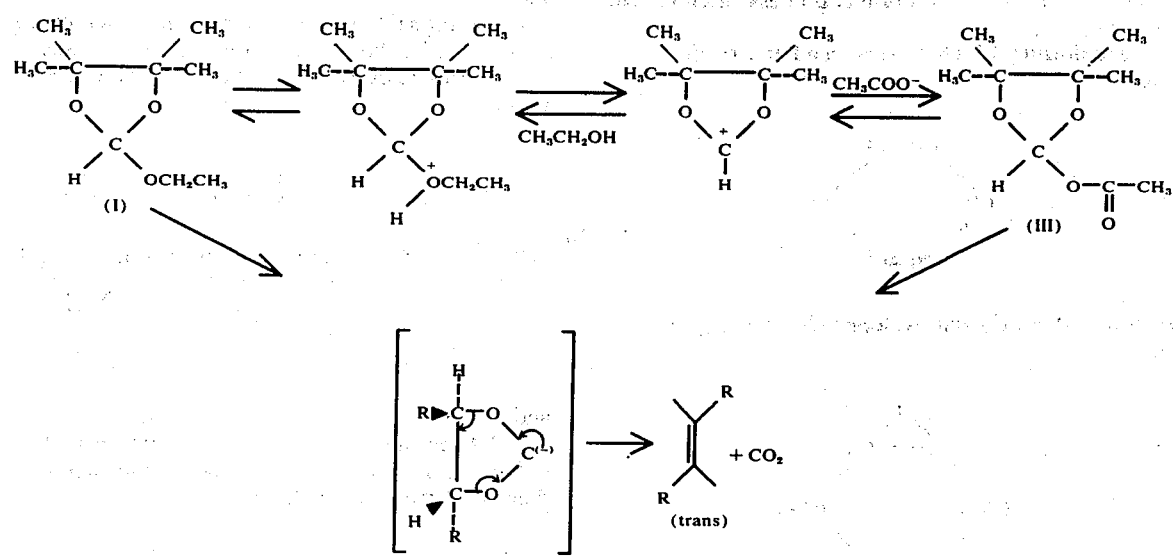

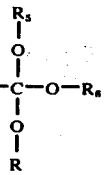

BRIEF DESCRIPTION OF THE DRAWINGS

FIG. 2 represents the NMR spectrum for trans-$\Delta^9$-isoambrettolide produced according to Example I, Part C.

FIG. 3 represents the Infrared spectrum for trans-$\Delta^9$-isoambrettolide produced according to Example I, Part C.

THE INVENTION

Figure 1:
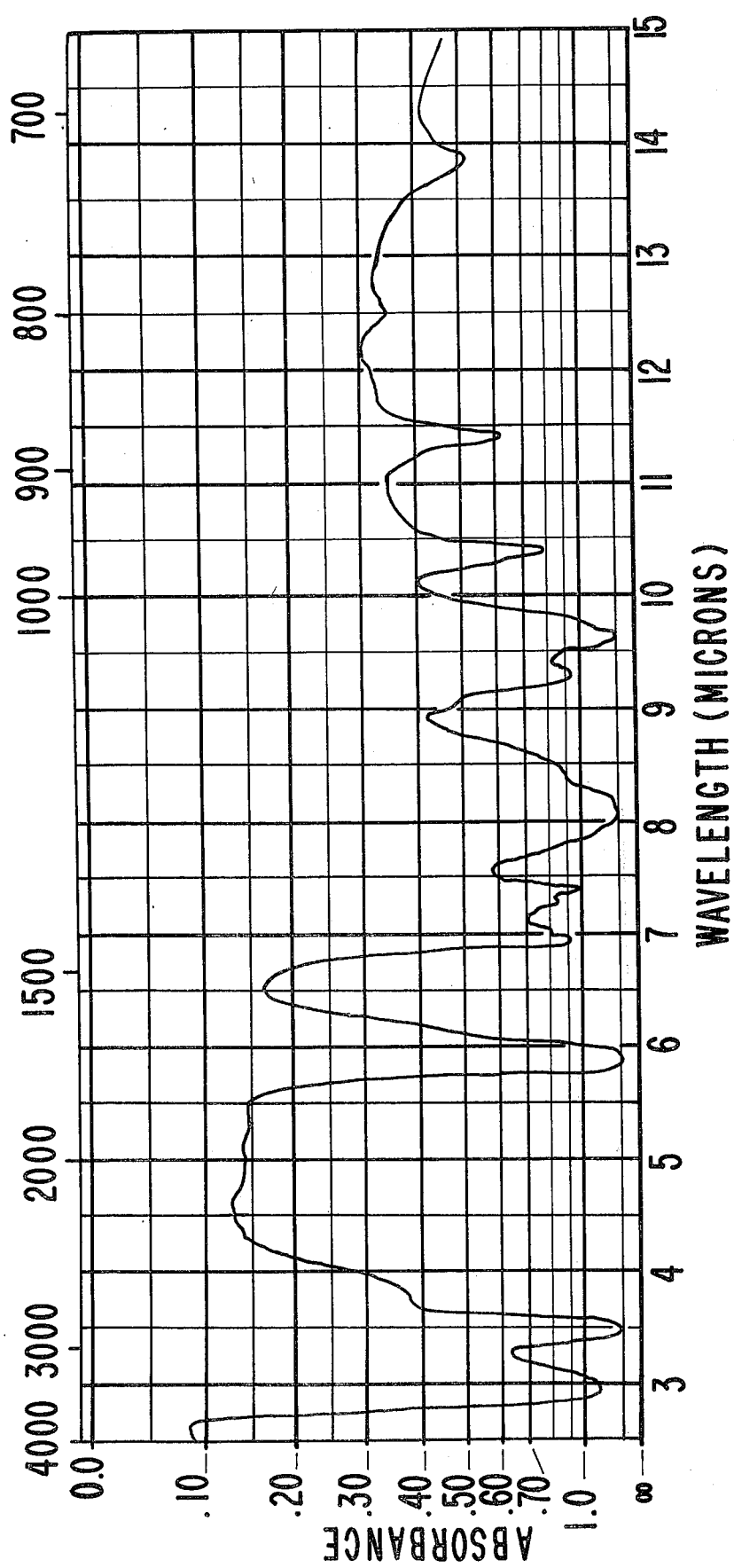
FIG. 1 represents the Infrared spectrum for bengalene acid methyl ester produced according to Example I, Part B.

My invention covers a process for producing substantially pure, and 100% trans-$\Delta^9$-isoambrettolide in a convenient, economical, three step process and also is intended to include a reaction intermediate, produced and used in one of the steps of said process.

More specifically, the process of my invention comprises the steps of:

i. admixing aleuritic acid having the formula:

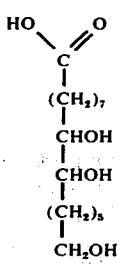

with a formylating agent which may be one of a trialkyl orthoformate having the structure:

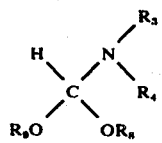

(wherein $R_5$, $R_6$, $R_7$ are the same or different lower alkyl) or a di-lower alkyl acetal of a di-lower alkyl formamide having the structure:

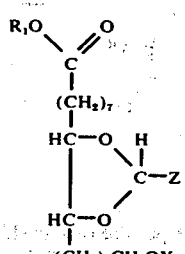

wherein $R_3$, $R_4$, $R_8$ and $R_9$ are the same or different lower alkyl, thereby producing a dioxolane derivative, a novel mixture represented by the structure:

wherein X represents H— and

H—C(=O)\ ;

wherein Z is selected from the group consisting of —$OR_2$ and

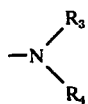

and $R_1$, $R_2$, $R_3$ and $R_4$ are the same or different lower alkyl;

ii. reacting the resulting dioxolane derivative with a lower alkanoic acid anhydride thereby forming a bengalene acid derivative mixture (100% trans isomer) having the generic structure:

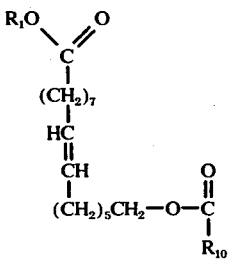

wherein $R_{10}$ is hydrogen and lower alkyl; and iii. heating the resulting trans bengalene acid derivative in the presence of a distillation aid, a transesterifying agent and a heat transfer material (such as glycerine, which has all three functions) thereby forming trans-$\Delta^9$-isoambrettolide having the structure:

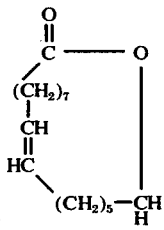

The first step of the process of my invention involving the formation of the dioxolane derivative is preferably carried out with an excess amount of trimethyl orthoformate (wherein $R_5$, $R_6$ $R_7$ are each methyl) or with the dimethyl acetal of dimethyl formamide (wherein $R_3$, $R_4$, $R_8$ and $R_9$ are each methyl). When using trimethyl orthoformate it is most preferred that the reaction be carried out at a temperature in the range of 40°–120° C and it is further preferred that a small quantity of protonic acid catalyst, such as para-toluene sulfonic acid be added to the reaction mass to lower the reaction temperature. When such is the case, at the termination of this first reaction, the reaction mass is neutralized using a small quantity of weak base such as sodium or potassium carbonate or sodium or potassium bicarbonate. As the reaction proceeds, methanol is formed as a reaction product and is steadily and controllably distilled from the reaction mass. The temperature of reaction requires that the pressure above the reaction mass be approximately atmospheric pressure. Lower pressures over the reaction mass give rise to lower required temperatures of reaction, but necessarily, somewhat longer periods of time for completion of reaction. When using the dimethyl acetal of dimethyl formamide it is preferable that the reaction be carried out at temperatures of between 100° and 120° C while steadily and controllably distilling off the methyl alcohol of reaction. Near the end of the reaction, the pressure above the reaction mass is reduced, preferably, to about 10 mm Hg pressure to remove all traces of the reaction product, methyl alcohol and excess reagent. In addition, the reaction is preferably carried out in the presence of an inert solvent, preferably methanol which is non-reactive with the formylating agent, e.g., the trimethyl orthoformate or the dimethyl acetal of dimethyl formamide.

The second reaction step involves the reaction of the dioxolane with a lower alkanoic acid anhydride. The anhydride reactant is preferably acetic anhydride, although propionic anhydride or butyric anhydride may also be used in addition to mixed anhydrides such as acetic-propionic anhydride, acetic-butyric anhydride and propionic-butyric anhydride. It is preferable that this reaction be carried out at atmospheric pressure at a temperature of between 120° and 180° C; more preferable are temperatures in the range of about 130°–160° C. It is also preferred that the time of reaction be between 3 and 7 hours. The reaction may be carried out successfully at lower temperatures and pressures below atmospheric above the reaction mass. At the end of the reaction, the reaction mass is "degassed" in order to remove the last traces of excess acetic anhydride so that the resulting bengalene acid "trans" derivative may be easily cyclized.

The resulting bengalene acid "trans" derivative is then cyclized to form the trans-$\Delta^9$-isoambrettolide preferably by heating the bengalene acid derivative in the presence of an alkali metal methoxide or hydroxide, such as potassium hydroxide or sodium hydroxide or sodium methoxide or an alkali metal carbonate, such as sodium carbonate or potassium carbonate, at a temperature in the range of 160°–220° C; preferably in the presence of a large excess of distillation aid, transesterifying agent and heat transfer medium, such as glycerine. During the heating process, the pressure over the reaction mass is reduced to about 30 mm Hg, while the desired trans-$\Delta^9$-isoambrettolide is continuously and controllably removed from the reaction mass. The desired product is collected as an oil layer above a layer of glycerine. The oil is pure or substantially pure trans-$\Delta^9$-isoambrettolide which can subsequently be used to enhance or augment perfume formulations and perfumed articles.

Thus, the product prepared by the process of the present invention has a highly desirable and useful odor characterized as a musk odor and usually thought of as the animal note in perfumes. The trans-$\Delta^9$-isoambrettolide is utilized as a component of perfume compositions and perfumed articles such as soap and detergents to promote musk fragrances. Perfume compositions containing from about 1.0 percent to about 50.0 percent of these musk odorants by weight based on the active fragrance ingredients before dilution are desirable and useful.

The following examples will illustrate in detail the manner in which the invention may be practiced. It will be understood, however, that the invention is not confined to the specific limitations set forth in the individual examples but rather to the scope of the appended claims.

EXAMPLE I

Preparation of Dioxolane Intermediate

Part A:

Into a 1 liter reaction flask equipped with stirrer, thermometer and heating mantle is added 304 g of aleuritic acid, 100 g Primol and 318 g trimethyl orthoformate. The reaction mass is heated to 75°–101° C over a period of 8 hours while removing methanol. 1 Gram of para-toluene sulfonic acid is then added to the reaction mass.

2 Grams NaHCO$_3$ is then added to the reaction mass in order to neutralize same. Then the excess trimethyl orthoformate is recovered at a vapor temperature of 25°–31° C and a pot temperature of 120°–135° C under vacuum. NMR and Infrared analyses confirm that the product formed is a mixture having the structure:

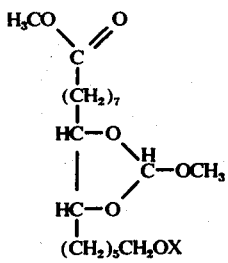

wherein X is H— and

PART B: PREPARATION OF BENGALENE ACID DERIVATIVE MIXTURE (100% TRANS)

The dioxolane derivative produced in Part A is intimately admixed with 110 ml acetic anhydride and the resulting mixture is heated to a temperature of 135°–160° C and maintained at that temperature for a period of 5 hours. The reaction mass is then stripped of excess acetic anhydride and the resulting product is analyzed and determined by Infrared and NMR analyses to be trans bengalene acid derivative having the structure:

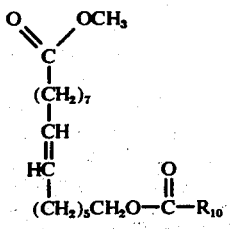

wherein R$_{10}$ is hydrogen and methyl.

FIG. 1 is the Infrared spectrum for the resulting compound.

Part C: Preparation of Trans-Δ$^9$-Isoambrettolide

The reaction product produced in Part B is admixed with 400 ml glycerine and 56 g 85% potassium hydroxide with stirring. The reaction mass is heated to a temperature in the range of 165°–180° C and maintained at that temperature for a period of 6 hours and product is removed at 30 mm Hg pressure and a vapor temperature of 152°–155° C. At the end of the 6 hour period, 300 ml glycerine and 5.0 g 85% potassium hydroxide is added to the reaction mass. This process is repeated 3 times at intervals of 3 hours, collecting a total of 8 fractions of pure trans-Δ$^9$-isoambrettolide which is confirmed by NMR and Infrared analyses to have the structure:

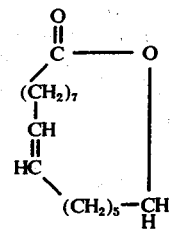

The NMR spectrum for the resulting compound is set forth in FIG. 2. The Infrared spectrum for the resulting compound is set forth in FIG. 3.

The NMR analysis is as follows:

| ppm | Interpretation |
| --- | --- |
| 1.30, 1.60 2.02 | methylene protons |
| 4.12 | $CH_2-\overset{O}{\underset{\|}{C}}-O-$ $CH_2-O-\overset{O}{\underset{\|}{C}}-$ |
| 5.37 | cyclic olefinic protons |

The Infrared analysis is as follows:
960 cm$^{-1}$, 1140, 1175, 1240, 1255, 1435, 1460, 1730, 2860, 2930.

EXAMPLE II

Part A: Preparation of Dioxolane Intermediate

Into a 2 liter reaction flask equipped with stirrer, thermometer and heating mantle is added 300 g methyl alcohol and 304 g aleuritic acid. The reaction mass is heated to 65° C and while maintaining the temperature at 65° C, 117 g of trimethyl orthoformate is added dropwise while simultaneously distilling off the methyl alcohol. When all of the trimethyl orthoformate is added, the reaction mass is heated to 110° C and the remainder of the methyl alcohol is distilled off. 131 Grams of dimethyl formamide dimethyl acetal having the formula:

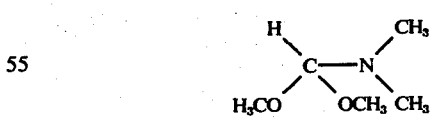

is then added to the reaction mass simultaneously distilling off additional methyl alcohol while maintaining the reaction mass temperature at 110° C and reducing the pressure over the reaction mass to 10 mm Hg.

Part B: Preparation of Bengalene Acid Derivative Mixture (100% Trans)

240 Grams of acetic anhydride is added to the reaction product produced in Part A, slowly distilling off the volatiles at atmospheric pressure, while maintaining the reaction mass temperature at 150° C. 100 Grams of methanol is added to the reaction mass while simultaneously distilling off the volatiles, while maintaining the temperature of reaction at 120° C and atmospheric pressure. Infrared analysis confirms that the product produced is "trans" bengalene acid methyl ester.

Part C: Preparation of Trans-Δ⁹-Isoambrettolide

To the product produced in Part B, 100 grams of Primol and 1200 grams of glycerine is added. The reaction mass is maintained at a temperature of 195°–205° C and trans-Δ⁹-iso-ambrettolide is distilled at a vapor temperature of 187°–190° C at 30 mm Hg. When the trans-Δ⁹-isoambrettolide stops distilling, 25 g of a 25% sodium methylate solution in methyl alcohol is added and trans-Δ⁹-isoambrettolide is continued to be distilled off at 205°–210° C at 30 mm Hg pressure. Infrared and NMR analyses confirm that the resulting product is trans-Δ⁹-isoambrettolide. The trans-Δ⁹-isoambrettolide thus produced is then admixed with 2 drops acetic acid and 25% Flexol 10—10 (di-iso-decyl-phthalate) and fractionally distilled yielding the following fractions and distillation data:

| Fraction No. | Vapor Temperature (° C) | Liquid Temperature (° C) | Pressure mm Hg | Weight of Fraction (g) |
|---|---|---|---|---|
| 1 | 118–122 | 144–147 | .2 | 14 |
| 2 | 124 | 150 | .2 | 14 |
| 3 | 127 | 153 | .2 | 16 |
| 4 | 131 | 157 | .18 | 15 |
| 5 | 132 | 159 | .19 | 15 |
| 6 | 133 | 166 | .15 | 17 |
| 7 | 113 | 184 | .15 | 15 |
| 8 | 200 | 238 | .18 | 15 |

EXAMPLE III

Perfume Composition

A perfume composition is prepared by admixing the following ingredients in the indicated proportions:

| Ingredient | Parts by Weight |
|---|---|
| Geranium Algerian | 100 |
| Clovebud Oil | 100 |
| Cassia | 30 |
| Labdanum resin | 60 |
| Castoreum absolute | 10 |
| Sandalwood Oil E.I. | 50 |
| Cedarwood | 150 |
| Ionone residues | 30 |
| Vetivert Oil | 20 |
| Benzyl benzoate | 150 |
| Terpineol | 150 |
| Trans-Δ⁹-isoambrettolide produced according to Example I | 150 |
| Total | 1000 |

This perfume composition is found to have a desirable musk fragrance quality.

EXAMPLE IV

Perfume Composition

A perfume composition is prepared by admixing the following ingredients in the indicated proportions:

| Ingredient | Parts by Weight |
|---|---|
| Geranium Algerian | 100 |
| Clovebud Oil | 100 |
| Cassia | 30 |
| Labdanum resin | 60 |
| Castoreum absolute | 10 |
| Sandalwood Oil E.I. | 50 |
| Cedarwood Oil | 150 |
| Ionone residues | 30 |
| Vetivert Oil | 20 |
| Benzyl benzoate | 150 |

-continued

| Ingredient | Parts by Weight |
|---|---|
| Terpineol | 150 |
| Trans-Δ⁹-isoambrettolide produced according to Example II | 150 |
| Total | 1000 |

This perfume composition is found to have a desirable musk fragrance quality.

EXAMPLE V

Soap Composition

A total of 100 g of soap chips are mixed with 1 gram of the perfume composition prepared in Example III until a substantially homogeneous composition is obtained. This homogeneous mixture is pressed into a bar having a desirable musk scent.

What is claimed is:

1. A mixture of dioxolane derivatives of aleuritic acid having the structure:

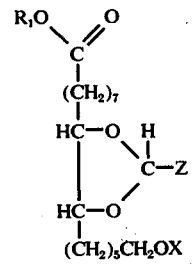

wherein X represents H— and

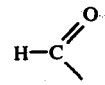

and wherein Z is selected from the group consisting of —OR₂ and

and R₁, R₂, R₃ and R₄ are the same or different lower alkyl.

2. The compound of claim 1 wherein each of R₁, R₂, R₃ and R₄ is methyl.

3. The compound of claim 1 wherein Z is —OR₂.

4. The compound of claim 1 wherein Z is

* * * * *